(12) United States Patent
El-Ayoubi et al.

(10) Patent No.: US 9,993,243 B2
(45) Date of Patent: Jun. 12, 2018

(54) FINGER-MOUNTED SURGICAL INSTRUMENTS AND METHODS OF USE

(71) Applicant: Edwards Lifesciences Corporation, Irvine, CA (US)

(72) Inventors: L'Emir Ahmad El-Ayoubi, Bad Bevensen (DE); Mark Dehdashtian, Irvine, CA (US); Teodoro S. Jimenez, Irvine, CA (US); Yoon H. Kwon, Mission Viejo, CA (US); Norma A. Garcia, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 12 days.

(21) Appl. No.: 14/845,709

(22) Filed: Sep. 4, 2015

(65) Prior Publication Data

US 2016/0066903 A1    Mar. 10, 2016

Related U.S. Application Data

(60) Provisional application No. 62/048,167, filed on Sep. 9, 2014.

(51) Int. Cl.
*A61B 17/04* (2006.01)
*A61B 17/02* (2006.01)
(Continued)

(52) U.S. Cl.
CPC .......... *A61B 17/0485* (2013.01); *A61B 17/02* (2013.01); *A61B 17/12* (2013.01);
(Continued)

(58) Field of Classification Search
CPC ..... A61B 17/02; A61B 17/0485; A61B 17/12; A61B 17/122; A61B 17/3201;
(Continued)

(56) References Cited

U.S. PATENT DOCUMENTS

| 79,703 A | * | 7/1868 | Stewart | A47J 17/02 30/123.5 |
| 1,601,560 A | * | 9/1926 | Codman | B26B 27/007 30/232 |

(Continued)

FOREIGN PATENT DOCUMENTS

| DE | 4136861 C2 | 12/1994 |
| DE | 19728139 A1 | 1/1999 |

(Continued)

OTHER PUBLICATIONS

International Search Report, dated May 26, 2011.

*Primary Examiner* — Kathleen Holwerda
(74) *Attorney, Agent, or Firm* — Guy Cumberbatch (57) ABSTRACT

A device is described which has an instrument portion secured to a sleeve/cuff portion, where the sleeve/cuff portion is configured to receive a portion of user's finger therein and to radially compress onto the user's finger to hold the instrument portion thereon. The present invention is particularly well suited for use in minimally invasive surgical procedures. The present invention also teaches a method of forming a knot in suture material as well as other techniques for treating patients.

9 Claims, 8 Drawing Sheets

(51) Int. Cl.
*A61B 17/12* (2006.01)
*A61B 17/122* (2006.01)
*A61B 17/00* (2006.01)
*A61B 17/28* (2006.01)
*A61B 17/3201* (2006.01)
*A61B 17/3211* (2006.01)

(52) U.S. Cl.
CPC ......... *A61B 17/122* (2013.01); *A61B 17/2841* (2013.01); *A61B 17/3201* (2013.01); *A61B 17/3211* (2013.01); *A61B 2017/00438* (2013.01); *A61B 2017/0474* (2013.01); *A61B 2017/12004* (2013.01); *A61B 2017/2837* (2013.01)

(58) Field of Classification Search
CPC ...... A61B 17/3211; A61B 2017/00438; A61B 42/00; A61B 42/20; A61B 2017/0474; A61B 2017/0475; B26B 27/00; B26B 27/007
USPC ........... 606/157, 158, 174, 205–211; 30/232; 289/17
See application file for complete search history.

(56) References Cited

U.S. PATENT DOCUMENTS

| | | | |
|---|---|---|---|
| 2,688,961 A * | 9/1954 | Thomas | A61F 5/50 128/880 |
| 3,805,793 A | 4/1974 | Wright | |
| 4,350,160 A | 9/1982 | Kolesov et al. | |
| 4,636,202 A | 1/1987 | Lowin et al. | |
| 4,641,652 A * | 2/1987 | Hutterer | A61B 17/0469 112/154 |
| 4,726,371 A * | 2/1988 | Gibbens | A61B 17/3201 30/232 |
| 4,976,032 A * | 12/1990 | Battaglia | B26B 27/007 30/298 |
| 5,080,663 A | 1/1992 | Mills et al. | |
| 5,084,058 A | 1/1992 | Li | |
| 5,133,723 A | 7/1992 | Li et al. | |
| 5,163,946 A | 11/1992 | Li | |
| 5,176,691 A | 1/1993 | Pierce | |
| 5,242,456 A | 9/1993 | Nash et al. | |
| 5,242,459 A | 9/1993 | Buelna | |
| 5,269,791 A * | 12/1993 | Mayzels | A61B 17/12013 606/1 |
| 5,334,200 A | 8/1994 | Johnson | |
| 5,374,275 A | 12/1994 | Bradley et al. | |
| 5,397,326 A * | 3/1995 | Mangum | A61B 17/0469 289/17 |
| 5,403,326 A | 4/1995 | Harrison et al. | |
| 5,403,330 A | 4/1995 | Tuason | |
| 5,423,837 A | 6/1995 | Mericle et al. | |
| 5,439,470 A | 8/1995 | Li | |
| 5,474,573 A | 12/1995 | Hatcher | |
| 5,540,704 A | 7/1996 | Gordon et al. | |
| 5,549,618 A | 8/1996 | Fleenor et al. | |
| 5,569,274 A | 10/1996 | Rapacki et al. | |
| 5,573,540 A | 11/1996 | Yoon | |
| 5,575,800 A | 11/1996 | Gordon | |
| 5,578,044 A | 11/1996 | Gordon et al. | |
| 5,601,574 A | 2/1997 | Stefanchik et al. | |
| 5,601,576 A | 2/1997 | Garrison | |
| 5,649,541 A * | 7/1997 | Stuckey | A61F 5/3761 128/880 |
| 5,662,664 A | 9/1997 | Gordon et al. | |
| 5,700,272 A | 12/1997 | Gordon et al. | |
| 5,713,910 A | 2/1998 | Gordon et al. | |
| 5,741,277 A | 4/1998 | Gordon et al. | |
| 5,741,279 A | 4/1998 | Gordon et al. | |
| 5,752,964 A | 5/1998 | Mericle | |
| 5,755,730 A | 5/1998 | Swain et al. | |
| 5,792,094 A | 8/1998 | Stevens et al. | |
| 5,810,877 A | 9/1998 | Roth et al. | |
| 5,827,300 A | 10/1998 | Fleega | |
| 5,836,956 A | 11/1998 | Buelna et al. | |
| 5,860,992 A | 1/1999 | Daniel et al. | |
| 5,885,238 A | 3/1999 | Stevens et al. | |
| 5,891,159 A | 4/1999 | Sherman et al. | |
| 5,891,160 A | 4/1999 | Williamson, IV et al. | |
| 5,906,577 A | 5/1999 | Beane et al. | |
| 5,925,064 A * | 7/1999 | Meyers | A61B 17/062 606/205 |
| 5,928,224 A | 7/1999 | Laufer | |
| 5,928,250 A | 7/1999 | Koike et al. | |
| 5,972,020 A | 10/1999 | Carpentier et al. | |
| 5,984,939 A | 11/1999 | Yoon | |
| 6,015,427 A | 1/2000 | Mueller et al. | |
| 6,045,561 A * | 4/2000 | Marshall | A61B 17/0469 606/139 |
| 6,047,700 A | 4/2000 | Eggers et al. | |
| 6,056,760 A | 5/2000 | Koike et al. | |
| 6,132,439 A | 10/2000 | Kontos | |
| 6,149,660 A | 11/2000 | Laufer et al. | |
| 6,152,934 A | 11/2000 | Harper et al. | |
| 6,162,233 A | 12/2000 | Williamson, IV et al. | |
| 6,165,183 A | 12/2000 | Kuehn et al. | |
| 6,183,484 B1 | 2/2001 | Matsutani et al. | |
| 6,260,552 B1 | 7/2001 | Mortier et al. | |
| 6,298,489 B1 * | 10/2001 | Cox | A41D 19/01594 2/160 |
| 6,312,447 B1 | 11/2001 | Grimes | |
| 6,511,488 B1 | 1/2003 | Marshall et al. | |
| 6,626,930 B1 | 9/2003 | Allen et al. | |
| 6,860,890 B2 | 3/2005 | Bachman et al. | |
| 8,562,632 B2 | 10/2013 | Jakoubek | |
| 2002/0049458 A1 | 4/2002 | Singhatat | |
| 2003/0220659 A1 | 11/2003 | Schmieding et al. | |
| 2004/0059350 A1 | 3/2004 | Gordon et al. | |
| 2004/0158125 A1 | 8/2004 | Aznoian et al. | |
| 2004/0193211 A1* | 9/2004 | Voegele | A61B 5/6826 606/205 |
| 2004/0231167 A1* | 11/2004 | Miklos | A61B 17/0467 30/298 |
| 2004/0254598 A1 | 12/2004 | Schumacher et al. | |
| 2004/0260281 A1* | 12/2004 | Baxter, III | A61B 18/14 606/41 |
| 2006/0190016 A1 | 8/2006 | Onuki et al. | |
| 2007/0156172 A1 | 7/2007 | Alvarado | |
| 2007/0219566 A1 | 9/2007 | Gambale | |
| 2008/0097479 A1 | 4/2008 | Boehlke et al. | |
| 2008/0243178 A1* | 10/2008 | Oren | A61B 17/0483 606/210 |
| 2012/0265222 A1* | 10/2012 | Gordin | A61B 17/06166 606/148 |

FOREIGN PATENT DOCUMENTS

| | | |
|---|---|---|
| DE | 19725739 C1 | 4/1999 |
| EP | 0706779 B1 | 5/2000 |
| WO | 9408515 A1 | 4/1994 |
| WO | 9515715 A1 | 6/1995 |
| WO | 9519139 A1 | 7/1995 |
| WO | 9529636 A1 | 11/1995 |
| WO | 9711642 A1 | 4/1997 |
| WO | 9727893 A1 | 8/1997 |
| WO | 9811825 A1 | 3/1998 |
| WO | 9857585 A1 | 12/1998 |
| WO | 99/00059 A1 | 1/1999 |
| WO | 99/13777 A1 | 3/1999 |
| WO | 00/03759 A2 | 1/2000 |
| WO | 0059382 A1 | 10/2000 |
| WO | 0060995 A2 | 10/2000 |
| WO | 0069342 A3 | 4/2001 |

* cited by examiner

FINGER-MOUNTED SURGICAL INSTRUMENTS AND METHODS OF USE

BACKGROUND OF THE INVENTION

Surgical instruments such as scalpels, clamps, suturing devices, knot pushers, etc., are commonly used in various types of surgery, including conventional surgeries as well as minimally invasive surgeries. Minimally invasive surgical techniques have emerged as an alternative to conventional surgical techniques to perform a plurality of surgical procedures. Minimally invasive procedures differ from conventional surgical procedures in that a plurality of devices may be introduced into the body through a small incision. As a result, trauma to the body is greatly reduced, thereby decreasing the recovery time of the patient.

Many conventional surgical procedures have been performed using minimally invasive techniques. One challenge presented when performing a surgical procedure is to provide the surgeon or other user with the ability to firmly hold the surgical instrument during its use, with reduced chance of the user losing grasp of the surgical instrument while also providing the user with effective control of the surgical instrument, especially the distal end thereof which is typically the "functional" end of the instrument which actually interacts with the patient's tissue or otherwise performs the procedure.

One challenge during surgeries, including minimally invasive techniques, is to position and apply sutures to an area of interest. Commonly, a suture will be required to approximate at least two pieces of tissue. In conventional surgical techniques, the surgeon will approximate the tissue pieces by forcing a needle and suture material through various portions of the tissue to be approximated, and tying a knot in the suture material resulting in approximation. However, even in conventional surgical techniques the user's access to the tissue to be sutured can be limited and/or involve small/delicate tissue requiring fine operational movement of the instrument. In minimally invasive surgical techniques, the surgeon's access to the approximation site can be greatly reduced. Commonly, a surgical device will attach the suture material to the tissue. The surgeon will remotely form a knot in the suture material and advance the knot to the area of interest with a "knot pusher," thereby approximating the tissue. Thereafter, the knot pusher is removed from the body and a suture cutting device is inserted to cut the surplus suture material.

Several knot pushing devices are known. These devices permit an operator to push suture knots which have been formed extracorporeally towards tissue to be sutured. For example, U.S. Pat. No. 5,769,863, issued to Garrison et al., discloses a surgical knot pusher having an elongated body connected to a pushing head. The pushing head engages a portion of suture material containing a knot and is advanced to the area of interest, thereby "throwing" the knot. Once the suture knot is placed the knot pushing device is removed and a cutting element is introduced into the body and cuts the remaining suture material. The remaining suture material is then removed. Another example of a knot pusher is presented in U.S. Pat. No. 6,860,890, entitled "Surgical Knot Pushing Device and Method of Use," which discloses a system using an elongated catheter-like device capable of intracorporeally positioning and applying a suture knot to an area of interest via minimally-invasive surgical openings. The knot pushing system allows the operator to cut and remove surplus suture material using the knot pushing device.

Many medical procedures are delicate procedures involving small and/or enclosed spaces where a user may only be able to advance the tips of his/her fingers. Moreover, it may be desirable to provide the user with devices and methods which provide tactile feedback that is stronger than that provided by larger hand-held or machine-held devices.

BRIEF SUMMARY OF THE INVENTION

The present invention provides a system, device, and method for permitting a surgeon or other user to effectively perform surgical procedures, including suturing, knot tying, tissue cutting, tissue ablation, tissue approximation, suture cutting, etc., using one or more surgical instruments that can be easily held by the user, including where the user may hold multiple such instruments at the same time.

A device according to the invention has a finger attachment sleeve/cuff portion that securely fits on a digit (e.g., finger or thumb) of a user. The finger attachment sleeve portion is attached to an instrument portion which has an operational element (such as a cutting element, clamping element, knot pushing element, etc.) thereon, such as on the distal end of the instrument portion. The device of the present invention is optimized for use in minimally invasive surgical procedures wherein the surgeon's access to the area of interest is greatly reduced. For example, a knot pushing device of the present invention may be used to advance a plurality of bi-manually formed surgical knots utilized in conventional surgical procedures. The knot pushing device disclosed herein may be further used to sequentially advance multiple knots or "throws" to the repair area.

A surgical device according to an embodiment of the invention may comprise: a finger attachment sleeve portion which may comprise a radially expandable and/or radially compressible sleeve configured to slidingly receive and hold a digit of a user; and an instrument portion secured to the finger attachment sleeve. The instrument portion may comprise a knot pushing element configured to engage suture during a medical procedure, and the instrument portion may further comprise an elongated member having a grooved and/or curled distal end. The instrument portion may comprise an elongated body which is rigid or flexible. The instrument portion may comprise a knot positioning member. The sleeve may comprise a braided tubular structure that will radially expand when longitudinally compressed and/or will radially contract when longitudinally stretched. The sleeve may comprise an inner lumen of between 1 and 6 cm in inner length and/or between 1 and 3 cm in inner diameter. The instrument portion may comprise an elongated member secured to and extending from a distal end of the sleeve. The instrument portion may comprise a first shaft and a second shaft and a pivot joint rotatably connecting the first shaft and the second shaft, with a proximal end of the first shaft secured to the sleeve. The instrument portion may comprise a scissors, wherein the first shaft comprises a first blade portion at a first shaft distal end and the second shaft comprises a second blade portion at a second shaft distal end. The instrument portion may comprise a clamp, wherein the first shaft comprises a first clamp portion at a first shaft distal end and the second shaft comprises a second clamp portion at a second shaft distal end.

A surgical device according to the invention may comprise: a first finger attachment sleeve portion, which may comprise a radially expandable and radially compressible first sleeve configured to slidingly receive and hold a first digit of a user; a second finger attachment sleeve portion, which may comprise a radially expandable and radially compressible second sleeve configured to slidingly receive and hold a second digit of a user; and an instrument portion secured to the first finger attachment sleeve and to the second finger attachment sleeve. The instrument portion may comprise scissors comprising a first shaft and a second shaft and a pivot joint rotatably connecting the first shaft and the second shaft, wherein the first shaft comprises a first scissor blade at a distal end thereof and the second shaft comprises a second scissor blade at a distal end thereof, wherein a proximal end of the first shaft is secured to the first finger attachment sleeve, and/or a proximal end of the second shaft is secured to the second finger attachment sleeve. The instrument portion may comprise a surgical clamp comprising a first shaft and a second shaft and a pivot joint rotatably connecting the first shaft and the second shaft, wherein the first shaft comprises a first clamp portion at a distal end thereof and the second shaft comprises a second clamp portion at a distal end thereof, wherein a proximal end of the first shaft is secured to the first finger attachment sleeve and/or a proximal end of the second shaft is secured to the second finger attachment sleeve. The instrument portion may comprise a first shaft and a second shaft, wherein a proximal end of the first shaft is secured to the first finger attachment sleeve and/or a proximal end of the second shaft is secured to the second finger attachment sleeve, and the instrument portion may comprise a pivot joint rotatably connecting the first shaft to the second shaft.

Methods according to the invention may include methods of treating tissue using the devices described herein, which may comprise: advancing a first finger of a user into a surgical device, wherein the surgical device comprises a radially expandable and radially compressible first sleeve configured to slidingly receive and hold a digit of a user with an instrument portion secured to the first sleeve, wherein advancing the first finger of the user into the surgical device comprises slidingly advancing the first digit of the user into the surgical device until a tip of the digit is advanced to the distal end of an inner lumen of the first sleeve; advancing the first finger of the user toward a target site until the instrument portion is positioned at the target site; and performing a procedure at the target site with the instrument portion. Methods may further include advancing a second finger of a user into a surgical device, wherein the surgical device comprises a radially expandable and radially compressible second sleeve configured to slidingly receive and hold a digit of a user with an instrument portion secured to the second sleeve, wherein advancing the second finger of the user into the surgical device comprises slidingly advancing the second digit of the user into the surgical device until a tip of the digit is advanced to the distal end of an inner lumen of the second.

Other objects and further features of the present invention will become apparent from the following description when read in conjunction with the attached drawings.

DESCRIPTION OF THE PREFERRED EMBODIMENTS

Disclosed herein is a description of various illustrated embodiments of the invention. This description is not to be taken in a limiting sense, but is made merely for the purpose of illustrating the general principles of the invention. The section titles and overall organization of the present description are for the purpose of convenience only and are not intended to limit the present invention.

The surgical instruments and methods of the present invention are generally applicable to surgical procedures, including conventional and minimally invasive surgical procedures. The device and method disclosed herein are of particular value when a surgeon or other user is required to hold a surgical instrument while advancing the users finger/thumb into a confined operating area, such as into an incision in the patient, as is often the case during minimally-invasive surgeries. The device has particular relevance to surgical procedures such as securing cardiac valves and closure of anatomic structures (i.e., aorta, atrium, etc. . . . ). Those skilled in the art will appreciate, however, that the device and method are relevant to a variety of procedures.

As those skilled in the art will appreciate, the present invention may be utilized during conventional surgical procedures as well as other procedures, such as minimally-invasive surgical procedures. It is anticipated as being within the scope of the present invention to produce a surgical instrument capable of performing functions at various locations within a body.

Referring to FIGS. 1A-1E of the drawings, the device 10 comprises a distal end 12 and a proximal end 14. The device 10 has two main portions—a digit-grasping portion 16 and an instrument portion 18. The instrument portion 18 comprises a length 20, and has an operational element 22 thereon for performing functions, such as interacting with tissue and/or other devices (including sutures, implants, other surgical devices, etc.). The operational element 22 may be positioned anywhere on the instrument portion 18, although often it will be positioned on the instrument portion distal end 24, as in the embodiment of FIGS. 1A-1E. The instrument portion proximal end 26 is secured at an attachment point 28 to the digit-grasping portion distal end 30. Various methods of attachment are within the scope of the invention, including overmolding, thermal, adhesive and mechanical bonding.

The digit-grasping portion 16 has the digit-grasping portion distal end 30 and a digit-grasping portion proximal end 32. In the particular embodiment depicted the digit-grasping portion 16 is a sleeve or cuff defined by an elongated hollow structure having an outer surface 33, with a length 34 and a width 36. The digit-grasping portion 16 has a proximal opening 38 leading to an internal lumen 40 for slidingly receiving a digit (such as finger or thumb) of a user. The internal lumen 40 has an inner length 42 and inner diameter 44 sized and configured to slidingly receive and retain at least a distal portion of a surgeon's or other user's digit, e.g., thumb and/or finger(s) (index finger, middle finger, ring finger, pinky finger). The inner surface 46 of the digit-grasping portion 16 may be textured or otherwise configured for increased frictional contact with a user's digit when inserted therein.

The digit-grasping portion 16 may be a substantially tubular sleeve or cuff and formed with a substantially cylindrically, helically wound braid which permits the structure to elongate and narrow when subjected to longitudinally applied stretching forces and/or radially-applied compressive forces, and to shorten and thicken when subjected to longitudinally applied compressive forces and/or radially-applied expansion forces. Examples of such structures include the common biaxial braid, and known in the art for use in children's "finger trap" toys. As is known in the art, such a sleeve/cuff can be placed on a finger or thumb, and pulling on such a sleeve/cuff lengthens and narrows it. The greater the pull, the more the circumference narrows and hence the stronger the sleeve/cuff grips the finger or thumb. The sleeve can be removed from the finger/thumb by applying a longitudinally compressive force to the structure, such as by pressing longitudinally inward against a first (e.g., proximal) edge of the sleeve, which may be accompanied by simultaneously applying a longitudinally-inward-directed force against the opposing (e.g., distal) end of the sleeve.

Figures 1A, 1B:
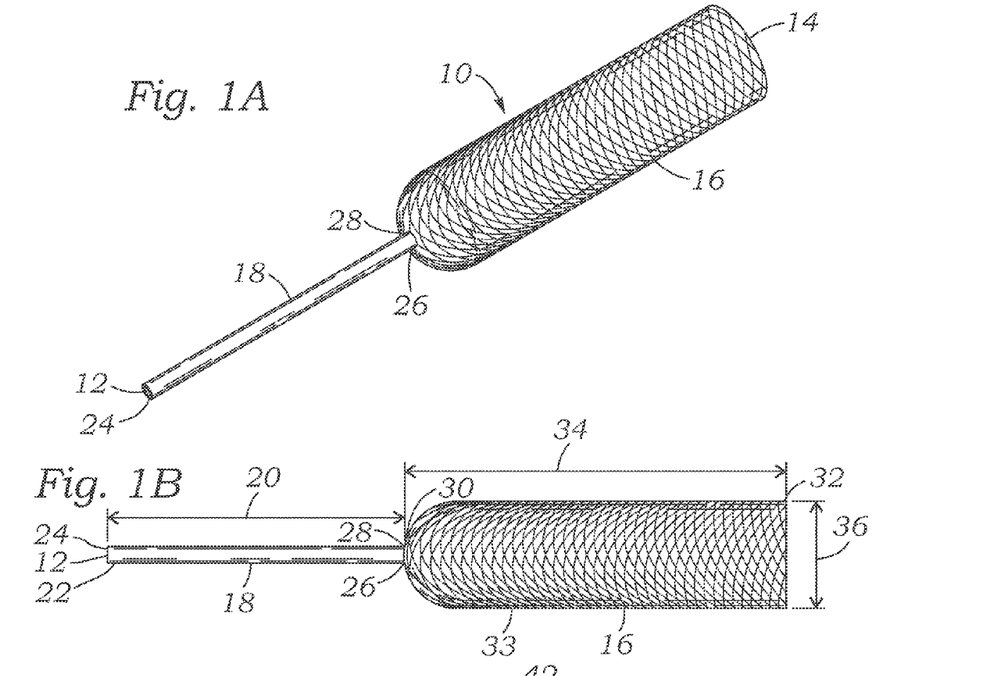
FIGS. 1A-1E depict perspective, side, side (cross-sectional), front, and back views of a surgical device according to an embodiment of the invention.
Figure 1C:
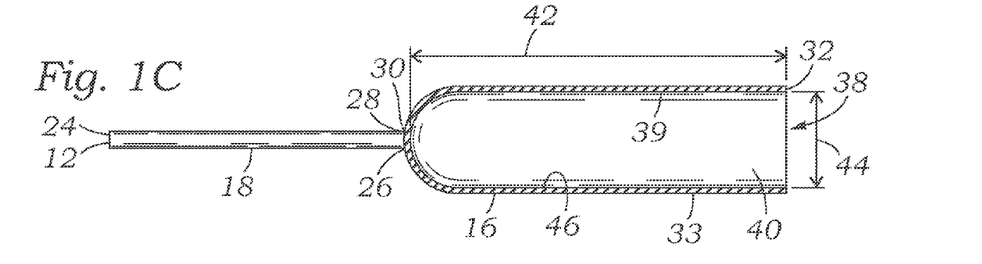
Figure 1D:
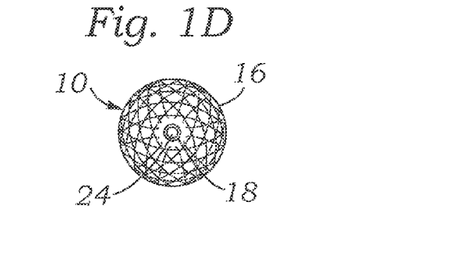
Figure 1E:
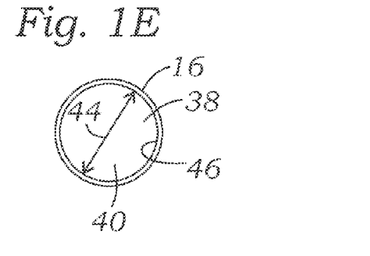
Figure 2A:
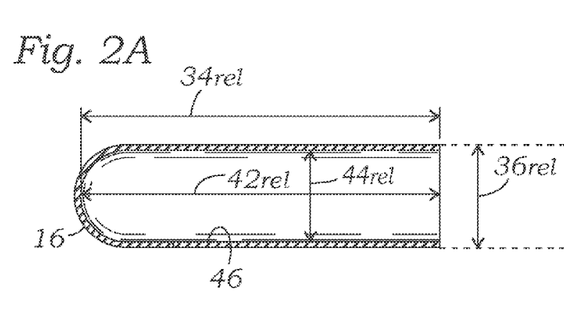
FIGS. 2A-2B depict side and proximal views of a digit-grasping portion of a surgical device in a relaxed configuration according to an embodiment of the invention.
Figure 2B:
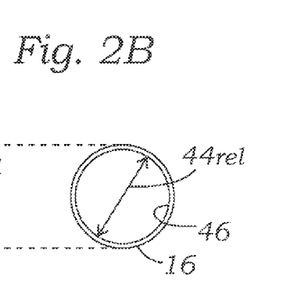

As depicted in FIGS. 2A-2B, the digit-grasping portion 16 may have a relaxed state with a length $34_r$, width $36_r$, inner length $42_r$, and inner diameter $44_r$. The relaxed state may be the state to which the digit grasping portion 16 is biased when not subject to external forces such as pulling, pushing, radial expansion, etc.

Figure 3A:
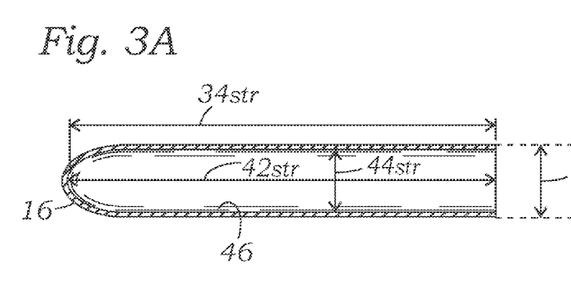
FIGS. 3A-3B depict side and proximal views of the digit-grasping portion of FIGS. 2A-2B in a shortened/expanded configuration.
Figure 3B:
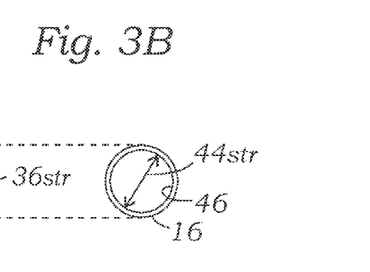

FIGS. 3A-3B depict the digit grasping portion 16 in a longitudinally stretched state, including length $34_s$, width $36_s$, inner length $42_s$, and inner diameter $44_s$. The stretched state can occur when the digit grasping portion 16 is subjected to elongating forces, such as when the device is pulled on one or both (e.g., distal and/or proximal) ends thereof, and/or radially compressive forces applied to the outer surface thereof. In the stretched state, the length $34_s$ and inner length $42_s$ are increased, and the width $36_s$ and inner diameter $44_s$ are decreased.

Figure 4A:
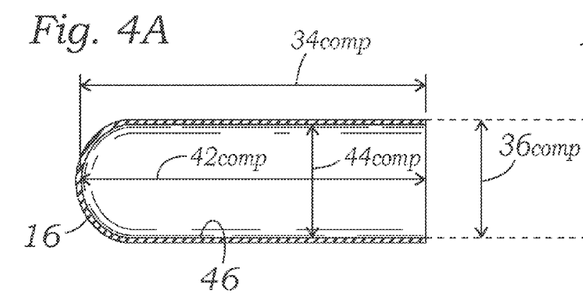
FIGS. 4A-4B depict side and proximal views of the digit-grasping portion of FIGS. 2A-2B in a lengthened/contracted configuration.
Figure 4B:
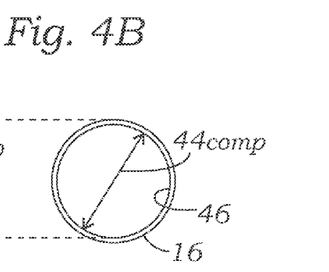

FIGS. 4A-4B depict the digit grasping portion 16 in a longitudinally compressed state, including length $34_c$, width $36_c$, inner length $42_c$, and inner diameter $44_c$. The compressed state can occur when the digit grasping portion 16 is subjected to shortening forces, such as when the device is pushed longitudinally inwardly at one or both (e.g., distal and/or proximal) ends thereof, and/or radially expansive forces applied to the inner surface (e.g., from the inner lumen) thereof. In the compressed state, the length $34_c$ and inner length $42_c$ are decreased, and the width $36_c$ and inner diameter $44_c$ are increased.

Note that in a preferred embodiment of the invention the sleeve/cuff in the relaxed state has an inner diameter somewhat smaller than an outer diameter of the digit (finger/thumb) to which the sleeve/cuff is attached, so that the inherent inward bias of the sleeve/cuff will compress against the user's digit to prevent inadvertent sliding off thereof. In such an embodiment, applying the sleeve/cuff to the digit may require the sleeve/cuff to be radially expanded/longitudinally shorted, such as may be achieved by pressing the user's finger into the inner lumen of the sleeve/cuff (thus applying longitudinally compressive force and radially expansive force to the sleeve/cuff). When the longitudinally compressive force is removed, the sleeve/cuff will bias back toward its relaxed state, thus gripping onto the user's finger/thumb. The gripping force becomes even stronger if device is subjected to pulling at either end. The device can be easily removed by applying inwardly-direct longitudinal force thereto, such as by applying a distally-directed force against the proximal end of the digit-grasping portion.

Devices according to the present invention may be manufactured with various dimensions, as required for particular applications. For example, preferred lengths for the distal knot pushing/creating segment may be from 1 cm to 20 cm. Preferred dimensions for the cuff/sleeve may include an inner lumen of cuff/sleeve of between 1 cm and 6 cm in internal length and between 1 cm and 3 cm in inner diameter.

Those skilled in the art will appreciate that the sleeve/cuff 16 may be manufactured from any one or more of a plurality of materials, including, for example, polymers, carbon, metals, etc. Similarly, the instrument portion 18 may be formed from various materials, such as metals (e.g., stainless steel, titanium, etc.), polymers, etc. Also, note that the instrument portion 18 of the present invention may contain one or more internal lumens, depending on the particular application.

Figure 5A:
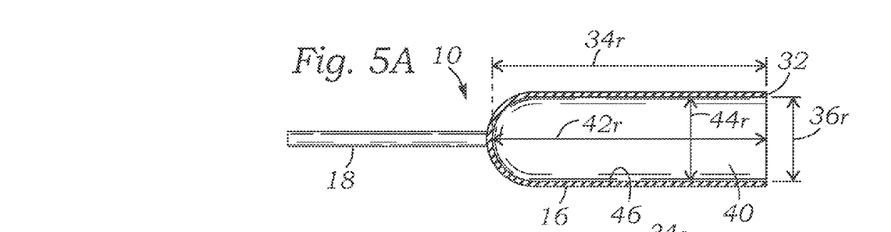
FIGS. 5A-5D depict side views, in partial cross-section, of a surgical device being placed upon and removed from a user's digit according to an embodiment of the invention.
Figure 5B:
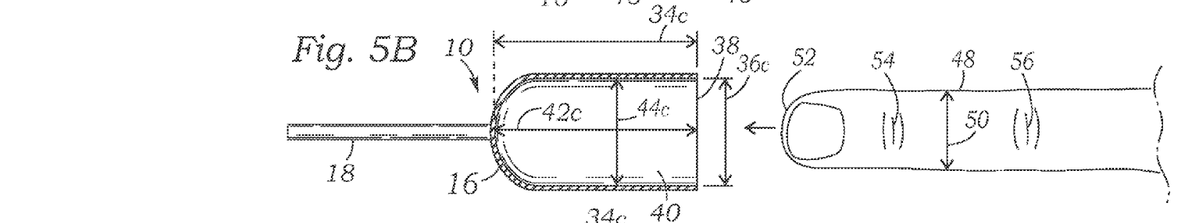
Figure 5C:
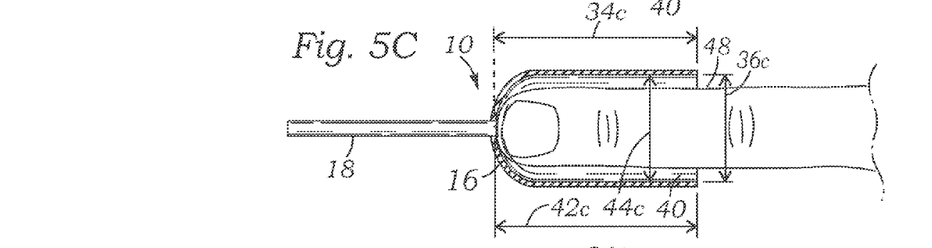
Figure 5D:
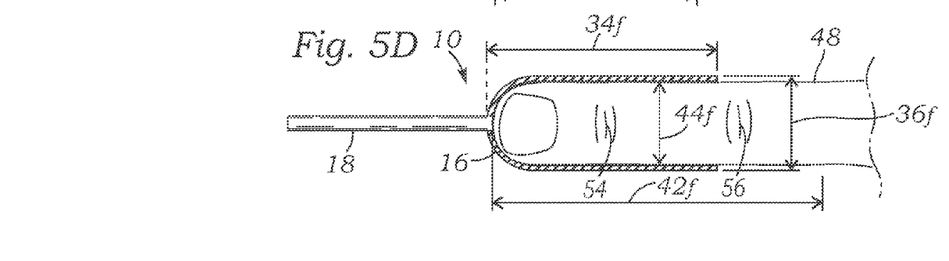

Referring now to FIGS. 5A-5D, a surgical device according to the invention can be easily secured to and removed from a user's finger or other digit. In FIG. 5A, the device 10 is depicted with the sleeve/cuff 16 in the relaxed state with outer length $34_r$, inner lumen length $42_r$, outer diameter $36_r$, and inner diameter $44_r$. The sleeve/cuff 16 may be longitudinally compressed to expand its diameter such that the inner diameter $44_c$ is larger than a diameter 50 of the user's finger, as depicted in FIG. 5B, with the user's finger 48 being advanced toward the proximal opening 38. The user's finger 48 or other digit can be advanced into the inner lumen 40 until the finger distal tip 52 is against or adjacent the distal end of the inner lumen 40. With the user's finger 48 or other digit fully advanced into the inner lumen 40, the longitudinal compressive force on the sleeve/cuff 16 can be released, whereupon the sleeve/cuff 16 biases toward a smaller diameter and securely engages around the user's finger 40 or other digit to secure the device 10 in place. The fastened diameter $44_f$ (or diameters where the diameter may vary along the length of the device) of the sleeve/cuff 16 when fastened to the user's finger 48, as depicted in FIG. 5D, approximates the diameter(s) 50 of the users finger 48. In the particular embodiment depicted, when secured to the user's finger 48 or other digit the sleeve/cuff 16 extends over the distal knuckle 54 to a position just distal of the proximal knuckle 56. Note, however, that other configurations are also within the scope of the invention, such as where the proximal end 38 of the sleeve/cuff 16 is positioned: (a) just proximally of the proximal end of the fingernail 58; (b) adjacent the distal knuckle; (c) adjacent the proximal knuckle; (d) between the distal knuckle and proximal knuckle; (e) proximal of the proximal knuckle; or (f) distal of the distal knuckle.

Figure 6A:
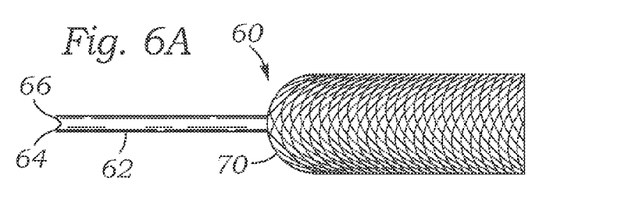
FIGS. 6A-6C depict side, front, and side (close-up) views of a knot pusher according to an embodiment of the invention.
Figure 6B:
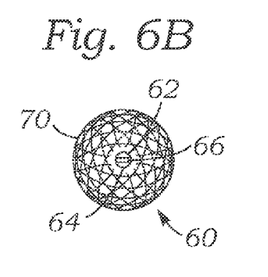
Figure 6C:
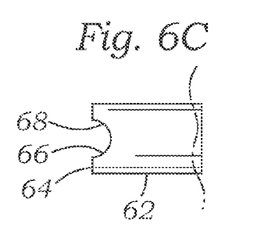
Figure 6D:
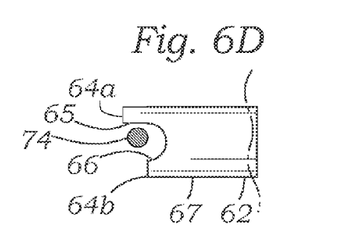
FIG. 6D depicts a side view (close-up) of an alternative embodiment of a knot pusher tip.

A knot pusher 60 according to an embodiment of the invention is depicted in FIGS. 6A-6B, with the knot pushing portion 62 having a distal face 64 with a groove 66 thereacross. The groove 66 is configured to receive suture therein to assist in advancing a knot into a surgical site in a patient. For example, the groove 66 may have a radius 68 of roughly 0.1 to 1 mm to smoothly and securely engage suture, as depicted in FIG. 6C. In another example of a tip depicted in FIG. 6D, the distal face has a first face portion 64a which extends distally more than the second face portion 64b, with a first portion inner side surface 65 extending past the second face portion 64b and presenting the surface 65 to engage against suture 74. For example, the first face portion 64a may extend 0.1 to 5 mm, or more, past the second face portion 64b, with the first portion inner side surface 65 having a corresponding length of 0.1 mm or more, such as between 0.1 and 5.0 mm, 0.5 and 3.0 mm, or 1.0 and 2.0 mm. For example, in embodiments of the invention the surface 65 has a length of 0.1 to 1.0 mm or even 0.1 to 0.5 mm. The tip configuration helps with catching/grabbing the suture 74. For example, a surgeon or other user can bring the first portion inner side surface 65 into engagement with the suture 74 and then advance the tip distally to position the suture 74 within the groove 66. If the surgeon or other user had difficulty initially positioning the first portion inner side surface 65 directly against the suture, the surgeon could first bring the lower surface 67 into engagement with the suture 74 (i.e., by pressing downward with the lower surface 67 against the suture 74), and then retract the tip proximally until the suture 74 slips distally along the lower surface 67 and across the second face portion 64b to engage against the first portion inner side surface 65 (with the suture movement likely being felt by the surgeon or other user via his/her fingertip). Once the suture was engaged against the first portion inner side surface (i.e., once the surgeon or other user felt the suture 74 engage against the first portion inner side surface 65), then the surgeon could advance the tip distally to position the suture 74 securely within the groove 66. Note that many different tip configurations are within the scope of the invention.

Figure 6E:
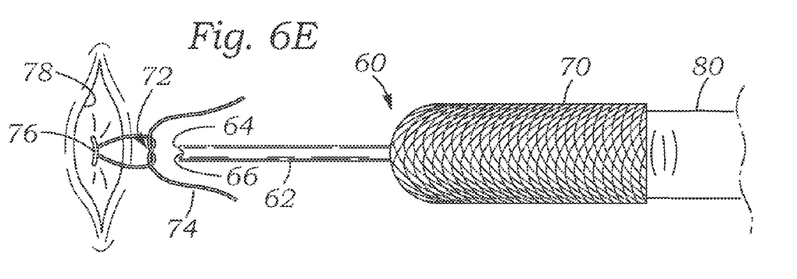
FIGS. 6E-6F depict the knot pusher of FIGS. 6A-6C being used to advance a suture knot into a surgical site.
Figure 6F:
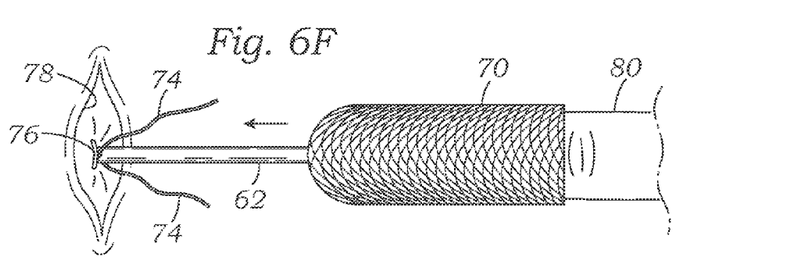

A digit-receiving sleeve/cuff 70 provides secure attachment to a surgeon or other user's finger or thumb. FIGS. 6E-6F depict the knot pusher 60 in use. The surgeon or other user can apply a knot loop 72 in suture 74 at a position outside of the surgical site 76 (e.g., outside the incision 78 leading to the surgical site 76). With the knot pusher 60 secured to the user's finger or other digit 80 via the sleeve/cuff 70, then engage the groove 66 of the distal face 64 against the knot loop 72 (FIGS. 6E-6F). The knot pusher 60 can then be distally advanced into the patient, with the knot loop 72 positioned in the groove 66 as the distal face 64 is advanced toward the surgical site. Pulling tension may be applied to the suture 74 (e.g., by the surgeon or other user) during knot advancement to assist in maintaining the knot loop on the distal face 64 and in the groove 66. Once the distal face 64 and knot loop 72 are positioned at the surgical site, the knot pusher 60 can be withdrawn, leaving the knot loop 72 in place at the surgical site. Note that the knot pusher 60 can also be useful in creating knots, such as there the knot pusher distal face is used to hold suture/knots in place while the surgeon or other user applies additional loops/knots to the suture.

Figure 7A:
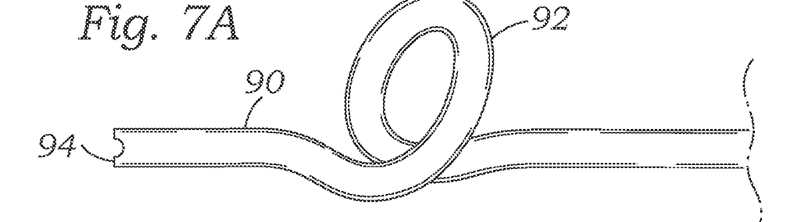
FIGS. 7A-7B depict side and front views of a helical knot pusher according to an embodiment of the invention.
Figure 7B:
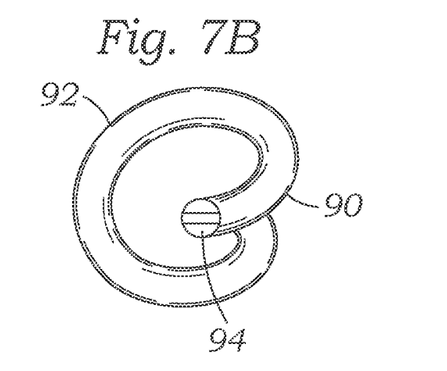

As depicted in FIGS. 7A-7B, a knot pusher according to an embodiment of the invention may include a knot pusher portion 90 having a helical twist 92 on the knot pusher portion 90 just proximal of the grooved distal face 94. The helical twist 92 can be used to form knots in suture. To form knots, a user can overlap lines of suture, and then use the helical twist 92 of the knot pusher portion 90 to hook one of the suture lines and pull it through a loop in the other suture line. Once a knot is loosely formed, the user can then advance the knot distally to the desired position by advancing the knot with the grooved distal face 94.

Figure 8:
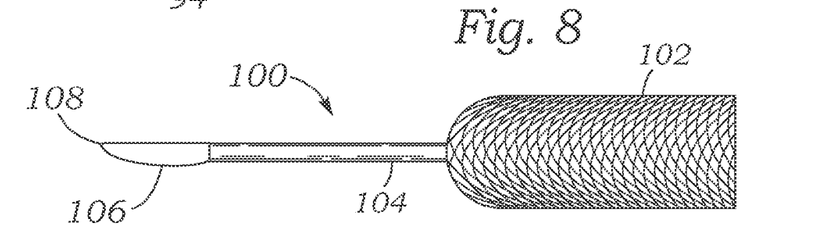
FIG. 8 depicts a side view of a scalpel according to an embodiment of the invention.

A cutting instrument 100 according to an embodiment of the invention is depicted in FIG. 8, with a sleeve/cuff portion 102 and an instrument portion 104 comprising a scalpel 106 or similar cutting implement at the distal end 108 thereof. Note that other positioning of the scalpel or similar cutting implement is also within the scope of the invention, such as on the side of the instrument portion 104.

Figure 9:
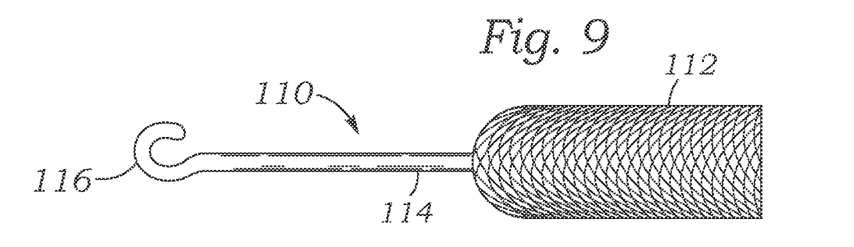
FIG. 9 depicts a side view of a surgical device having a hook at its distal end according to an embodiment of the invention.

A hooked surgical device 110 according to an embodiment of the invention is depicted in FIG. 9. The device 110 has a sleeve/cuff portion 112 and a distal portion 114 having a hook 116 thereon. The hook 116 may be used to engage and pull on various structures, such as surgical instruments/devices and/or body features (e.g., blood vessels, ligaments, etc.).

Figure 10:
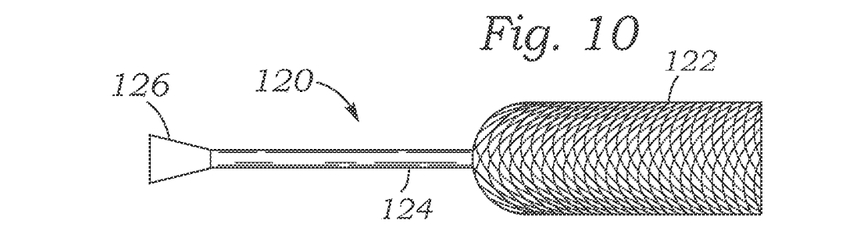
FIG. 10 depicts a side view of a surgical instrument having a blunt surface at its distal end according to an embodiment of the invention.

A blunt-ended surgical device 120 according to an embodiment of the invention is depicted in FIG. 10. The device 120 has a sleeve/cuff portion 122 and a distal portion 124 having a blunt-ended instrument 126 on the distal end thereof that can be used to press against various structures. For example, the blunt-ended instrument 126 can be used to push tissue structures out of the way during surgery.

Figure 11A:
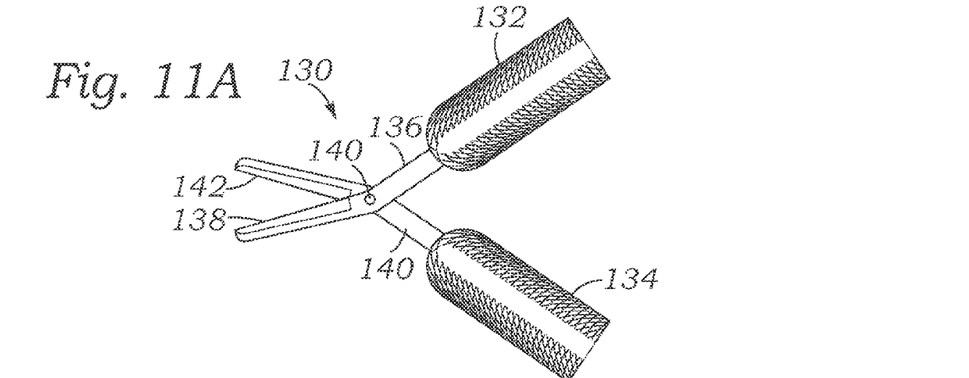
FIGS. 11A-11B depict side views of surgical scissors according to an embodiment of the invention.
Figure 11B:
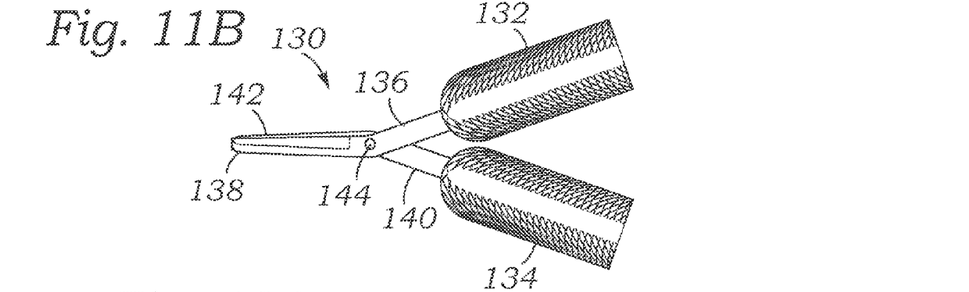

Surgical devices according to embodiments of the invention may comprise multiple sleeves/cuffs, such as in the embodiments of FIGS. 11A-11B and 12A-12B. Surgical scissors 130 according to an embodiment of the invention are depicted in FIGS. 11A-11B, with a first sleeve 132 receiving a user's finger and second sleeve 134 for receiving a user's thumb. The scissors have a first shaft 136 with the first sleeve 132 at the proximal end and a first scissor blade 138 at the distal end thereof, and a second shaft 140 with the second sleeve 134 at the proximal end and the second scissor blade 142 at the distal end thereof. The first shaft 136 is secured to the second shaft 140 at a pivot joint 144. Bringing the user's thumb and finger together will cause the first and second sleeves 132, 132 to move together, thus rotating the first and second scissor blades 138, 142 into engagement to cut tissue or suture or other materials.

Figure 12A:
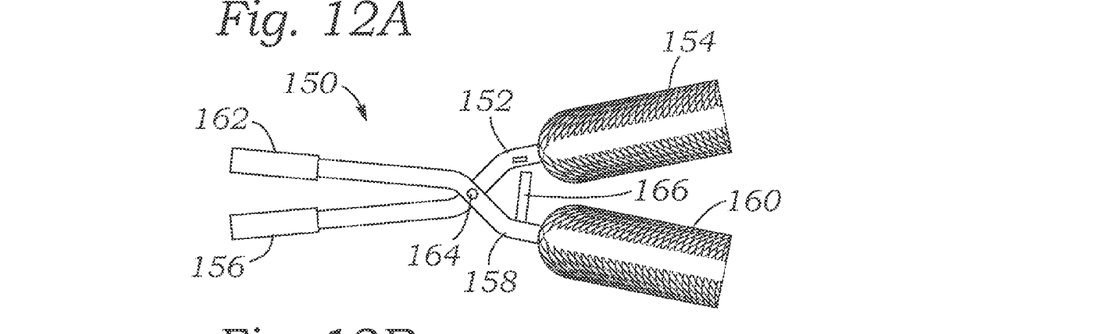
FIGS. 12A-12B depict side views of a surgical clamp according to an embodiment of the invention.
Figure 12B:
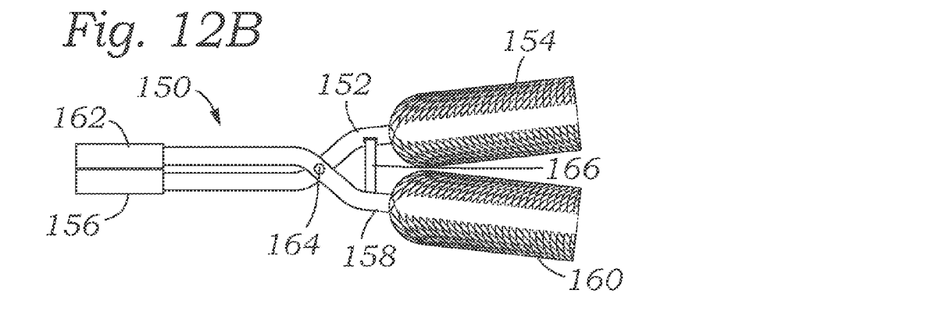

A surgical clamp 150 according to an embodiment of the invention is depicted in FIGS. 12A-12B. The clamp 150 comprises a first shaft 152 with a first sleeve 154 (e.g., for finger) at the proximal end and a first clamp portion 156 at the distal end thereof, and a second shaft 158 with a second sleeve 160 (e.g., for finger) at the proximal end and a second clamp portion 162 at the distal end thereof. The first shaft 152 is secured to second shaft 158 at a pivot joint 164. A lock 166 may be provided to hold the clamp 150 closed when desired.

Figure 13A:
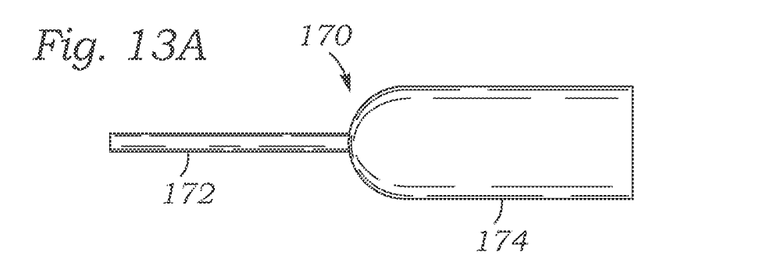
FIGS. 13A-13D depict side views, in cross section, of a device according to an embodiment of the invention.
Figure 13B:
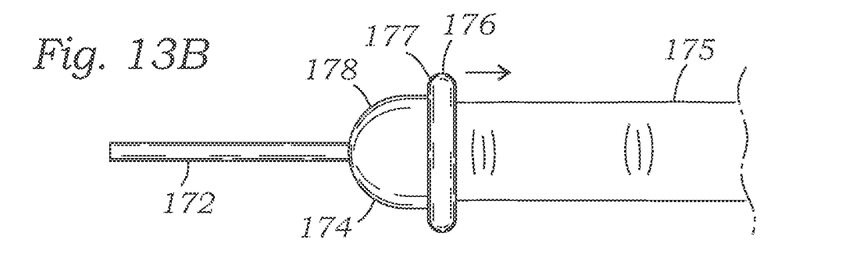
Figure 13C:
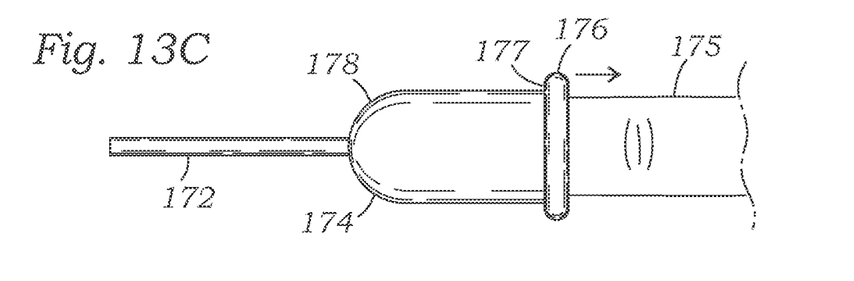
Figure 13D:
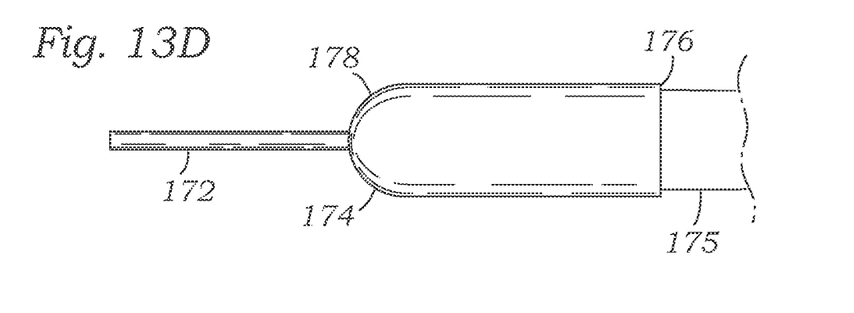

While woven/braided sleeve/cuff designs were previously discussed, other sleeve/cuff configurations are also within the scope of the invention. For example, as depicted in FIG. 13, a device 170 according to the invention may have an instrument portion 172 secured to a sleeve/cuff 174 formed from flexible material (which may be solid or meshed), such as rubber-like materials like ptfe, polymers (including polymeric braided mesh), thread-like cloth materials, and woven metal wire, that can stretch radially outwardly to receive a user's finger other digit but will then compress radially about the user's finger. Such devices 170 may be applied to a user's finger 175 or other digit by having the sleeve/cuff 174 rolled thereon, where before application the material of the open proximal end 176 of the sleeve/cuff 174 is rolled up toward the distal end 178 of the sleeve/cuff 174. As depicted in FIGS. 13C-13D, the rolled material 177 of the open proximal end 176 may be unrolled proximally onto the user's finger 175. The unrolling may be partial or complete, depending on the particular application. Removal of the device 170 from the user's finger 175 may be achieved by reversing the procedure of FIGS. 13C-13D (i.e., unrolling the sleeve/cuff 174 from the user's finger 175).

Figure 14A:
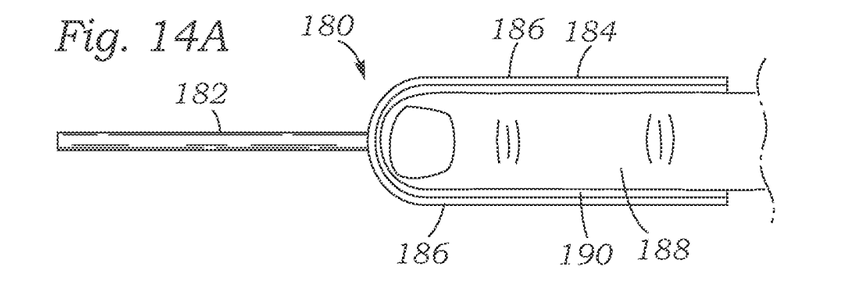
FIGS. 14A-14B depict side views, in cross section, of a device according to an embodiment of the invention.
Figure 14B:
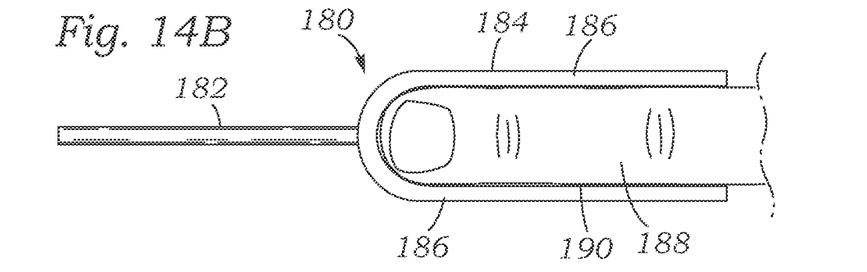

Other embodiments of sleeves/cuffs may include compressible and/or inflatable cuffs. As depicted in FIGS. 14A-14B, a device 180 may include an instrument portion 182 secured to a sleeve/cuff 184 having an inflatable liner 186. In FIG. 14A, the liner 186 is in a deflated condition. When inflated as depicted in FIG. 14B, the liner 186 extends radially inwardly into the lumen 190 of the sleeve cuff, thus engaging the user's finger 188 and securing the device thereto. When desired to remove the device from the user's finger, the liner 186 may be deflated, thus releasing the user's finger from the lumen 190 to permit the finger to be slidingly removed from the lumen 190.

In closing it is understood that the embodiments of the invention disclosed herein are illustrative of the principles of the invention. Accordingly, the present invention is not limited to that precisely as shown and described in the present invention.

What is claimed is:

1. A method of manipulating a surgical knot, comprising:
    providing a surgical knot pusher device, comprising:
        a finger attachment sleeve comprising a biaxial helically wound braided tubular structure configured to radially expand when longitudinally compressed and configured to contract when longitudinally stretched; and
        a rigid knot pusher secured to a distal tip of the finger attachment sleeve, wherein the knot pusher includes an elongated member that extends a length from the distal tip and terminates in a distal face with a groove thereacross, the groove being configured to receive a suture therein, and the elongated member forms a helical twist just proximal to the grooved distal face, the helical twist being formed by a helical bend in the elongated member;
    longitudinally compressing the finger attachment sleeve and inserting a digit of a user into the sleeve such that a proximal end of the sleeve is located at least proximal of a proximal end of the user's fingernail;
    permitting the finger attachment sleeve to contract to grip onto the digit of the user;
    hooking a first one of an overlapping pair of sutures in the helical twist and then pulling the first one of the sutures through a loop in a second one of the sutures to form a loose knot; and
    engaging and advancing the loose knot using the grooved distal face to a surgical site in a patient.

2. The method of claim 1, wherein the groove has a radius of between 0.1 to 1 mm.

3. The method of claim 1, wherein the groove divides the distal face into a first face portion and a second face portion.

4. The method of claim 3, wherein the first face portion extends distally farther than the second face portion, with a first face portion inner side surface extending past the second face portion and presenting a surface to engage against a suture.

5. The method of claim 4, further including bringing the first face portion inner side surface into engagement with the suture and then advancing the distal tip distally to position the suture within the groove.

6. The method of claim 4, further including bringing an outer surface of the elongated member into engagement with the suture, the outer surface being adjacent the second face portion, and then retracting the distal tip proximally until the suture slips distally along the outer surface and across the second face portion to engage against the first face portion inner side surface, then advancing the distal tip distally to position the suture within the groove.

7. The method of claim 4, wherein the first face portion extends distally between 0.1 and 5.0 mm farther than the second face portion.

8. The method of claim 7, wherein the first face portion extends distally between 0.5 and 3.0 mm farther than the second face portion.

9. The method of claim 8, wherein the first face portion extends distally between 1.0 and 2.0 mm farther than the second face portion.

\* \* \* \* \*